United States Patent
Gong et al.

(10) Patent No.: US 12,194,440 B2
(45) Date of Patent: Jan. 14, 2025

(54) SUPPORTED CORE-SHELL STRUCTURED ZnO CATALYST, AND PREPARATION METHOD AND USE THEREOF

(71) Applicant: TIANJIN UNIVERSITY, Tianjin (CN)

(72) Inventors: Jinlong Gong, Tianjin (CN); Yiyi Xu, Tianjin (CN); Sai Chen, Tianjin (CN); Chunlei Pei, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 606 days.

(21) Appl. No.: 17/542,215

(22) Filed: Dec. 3, 2021

(65) Prior Publication Data
US 2022/0088573 A1    Mar. 24, 2022

Related U.S. Application Data

(63) Continuation of application No. PCT/CN2020/127847, filed on Nov. 10, 2020.

(30) Foreign Application Priority Data

Jun. 30, 2020 (CN) ......................... 202010621436.8

(51) Int. Cl.
*B01J 23/06* (2006.01)
*B01J 21/04* (2006.01)
(Continued)

(52) U.S. Cl.
CPC ............... *B01J 23/06* (2013.01); *B01J 21/04* (2013.01); *B01J 35/397* (2024.01); *B01J 35/398* (2024.01);
(Continued)

(58) Field of Classification Search
CPC ........ B01J 23/06; B01J 35/398; B01J 35/397; B01J 21/04; B01J 37/0201; B01J 37/08;
(Continued)

(56) References Cited

U.S. PATENT DOCUMENTS 3,360,567 A * 12/1967 Johnson, Jr. ............. B01J 21/00
502/329
4,917,947 A * 4/1990 Kosha .................. G11B 5/7085
428/329
(Continued)

FOREIGN PATENT DOCUMENTS

CN    102898312 A * 1/2013 .......... C07C 209/26
CN    104971717 A    10/2015
(Continued)

OTHER PUBLICATIONS

Chatla Anjaneyulu et al., "Effect of Zn addition on the performance of Ni/Al2O3 catalyst for steam reforming of ethanol." Applied Catalysis A: General 519, pp. 85-98. (Year: 2016).*
(Continued)

*Primary Examiner* — Patricia L. Hailey (57) ABSTRACT

The present invention belongs to the technical field of supported catalysts, and discloses a supported core-shell structured ZnO catalyst, and a preparation method and use thereof. With $Al_2O_3$ as a support and ZnO as active sites, the catalyst is characteristic of a NiZn@ZnO core-shell structure, which consists of a NiZn alloy core and a ZnO shell. The preparation method comprises firstly dissolving $Ni(NO_3)_3 \cdot 6H_2O$ and $Zn(NO_3)_2 \cdot 6H_2O$ in deionized water; then impregnating $Al_2O_3$ with the solution described above, followed by uniform ultrasonic dispersion and complete drying; and finally the obtained solid is calcinated and reduced to obtain the target catalyst, which exhibits high activity, selectivity and stability. The catalyst can be used for the dehydrogenation of light alkanes to alkenes, especially in dehydrogenation of propane to propylene.

15 Claims, 8 Drawing Sheets

(51) Int. Cl.
- *B01J 35/30* (2024.01)
- *B01J 37/02* (2006.01)
- *B01J 37/08* (2006.01)
- *C07C 5/32* (2006.01)

(52) U.S. Cl.
CPC ........... *B01J 37/0201* (2013.01); *B01J 37/08* (2013.01); *C07C 5/322* (2013.01); *C07C 2521/04* (2013.01); *C07C 2523/06* (2013.01)

(58) Field of Classification Search
CPC ......... B01J 35/505; B01J 35/53; C07C 5/322; C07C 2521/04; C07C 2523/06; C22C 19/03
USPC ................ 502/329, 337, 342, 343; 585/654; 428/403; 420/441, 513
See application file for complete search history.

(56) References Cited

U.S. PATENT DOCUMENTS

| | | | | |
|---|---|---|---|---|
| 7,682,582 | B2* | 3/2010 | Morton | B01J 20/3458 423/230 |
| 11,351,521 | B2* | 6/2022 | Gong | B01J 23/8906 |
| 2005/0245621 | A1* | 11/2005 | Baijense | B01J 23/80 502/329 |
| 2014/0106260 | A1* | 4/2014 | Cargnello | B01J 21/066 502/262 |
| 2020/0231882 | A1* | 7/2020 | Sunkara | C10G 25/003 |
| 2020/0332127 | A1* | 10/2020 | Schilling | H01B 1/02 |

FOREIGN PATENT DOCUMENTS

| | | | | |
|---|---|---|---|---|
| CN | 105664951 | A | | 6/2016 |
| CN | 105921148 | A * | 9/2016 | B01J 23/62 |
| CN | 107876059 | A * | 4/2018 | B01J 23/80 |
| CN | 109647414 | A | | 4/2019 |
| CN | 110172668 | A | | 8/2019 |
| CN | 110614092 | A | | 12/2019 |
| CN | 11659404 | A | | 9/2020 |
| CN | 113398937 | A * | 9/2021 | B01J 23/80 |
| JP | 2008264761 | A | | 11/2008 |
| WO | 2015028529 | A1 | | 3/2015 |

OTHER PUBLICATIONS

English translation of Written Opinion for PCT/CN2020/127847. (Year: 2021).*
International Search Report of PCT/CN2020/127847.
Heggen, Marc et al., Formation of ZnO Patches on ZnPd/ZnO during Methanol Steam Reforming: A Strong Metal-Support Interaction Effect, The Journal of Physical Chemistry C, Apr. 27, 2016.
Wang, Weixing et al., Strong metal-support interactions between Ni and ZnO particles and their effect on the methanation performance of Ni/ZnO, Catalysis Science & Technology, Aug. 21, 2017.

* cited by examiner

ID CORE-SHELL STRUCTURED
SUPPORTED CORE-SHELL STRUCTURED ZnO CATALYST, AND PREPARATION METHOD AND USE THEREOF

CROSS-REFERENCE TO RELATED APPLICATIONS

This application is a bypass continuation application of PCT application No. PCT/CN2020/127847. This application claims priorities from PCT Application No. PCT/CN2020/127847, filed Nov. 11, 2020, and from the Chinese patent application 2020106214368 filed Jun. 30, 2020, the contents of which are incorporated herein in the entirety by reference.

TECHNICAL FIELD

The present invention belongs to the technical field of supported catalysts, and in particular, relates to a core-shell structured NiZn@ZnO catalyst supported on $Al_2O_3$, and a preparation method and use thereof.

BACKGROUND OF THE PRESENT INVENTION

Propylene is one of the important basic chemical raw materials for industrial production, and is mainly used to produce polypropylene, propylene oxide, acrylonitrile, and other products. In recent years, the global demand for propylene has greatly increased, which has promoted the rapid growth of its production capacity. In 2019, the total domestic production of propylene reached 33 million tons, a year-on-year increase of 8.75%. At present, the supply of propylene mainly comes from the by-products of cracking of naphtha to ethylene and catalytic cracking of petroleum. However, with the development of shale gas rich in light alkanes, the ethylene production process has begun to shift from naphtha cracking to non-co-production technologies for ethylene such as ethane steam cracking. As a result, the price of propylene rises. In addition, the high energy consumption, low selectivity, and shortage of oil resources of traditional processes cannot meet the increasing demand, prompting people to find more economical and efficient propylene production methods. As the price gap between propylene and propane has been expanding since 2016, the production capacity of propane dehydrogenation has increased significantly, and the technology of propane dehydrogenation to propylene (PDH) has shown broad prospects. In October 2013, Tianjin Bohua's propane dehydrogenation unit with an annual capacity of 600,000 tons was put into operation, and then propane dehydrogenation begun to be used in China. From 2014 to 2016, the capacity of propane dehydrogenation (including mixed alkanes) has increased at a rate of at least three units put into operation each year. By the end of 2017, the total capacity of propane dehydrogenation (containing mixed alkanes) in China reached 513.5 million tons, accounting for 15% of the total propylene capacity.

The reaction formula of propane dehydrogenation is as follows: $C_3H_8 \rightleftharpoons C_3H_6+H_2$, $\Delta H_{298K}$=124.3 KJ/g·mol. The reaction is a strong endothermic reaction controlled by thermodynamic equilibrium, and high temperature and low pressure conditions are conducive to the progress of the reaction. Supported $CrO_x$ and Pt catalysts are two important industrial catalysts, which have been applied to the industrial processes of propane dehydrogenation, i.e. Lummus' Catofin process and UOP's Oleflex process, respectively. The $CrO_x$ catalyst used in the Catofin process suffers from carbon deposition deactivation, so that the catalyst needs to be regenerated per 12 minutes on average, and $CrO_x$ also causes serious environmental pollution. The Pt-based catalyst used in the Oleflex process is excellent in activating the C—H bonds of alkanes, however, the application of Pt as noble metal is strongly limited by its expensive price. Therefore, cheap and environmentally friendly alternative catalysts are attracting widespread interests.

Among various metal oxides with catalytic activity, such as vanadium oxide, gallium oxide, iron oxide, zirconium oxide, etc., zinc oxide, which is abundant in reserves and cheap and easily accessible, is a promising candidate with its relatively high catalytic activity and selectivity. The current problem is that zinc oxide, as an active species, is prone to quick deactivation when exposed to the reducing reaction atmosphere during the propane dehydrogenation reaction. The mechanism of deactivation is the reduction of ZnO to metallic Zn sites caused by formation and desorption of $H_2O$ during the recombination of surface hydroxyl groups and zinc alkyls on ZnO sites during the dehydrogenation reaction, and the resulting, metallic Zn sites exhibit no activity for propane dehydrogenation and are easy to lose with a lower melting point.

SUMMARY OF THE PRESENT INVENTION

The present invention aims to solve the technical problem that the existing ZnO-based catalysts are prone to quick deactivation, and provides a supported core-shell structured ZnO catalyst and a preparation method and use thereof. The catalyst, cheap and non-toxic, exhibits high activity and high selectivity and excellent stability, breaking the limitation of quick deactivation and therefore the catalyst can be used in dehydrogenation of light alkanes to alkenes.

In order to solve the above technical problem, the present invention is implemented with the following technical scheme:

according to one aspect of the present invention, a supported core-shell structured ZnO catalyst is provided, with $Al_2O_3$ as a support and ZnO as active sites; a NiZn@ZnO core-shell structure, which consists of a NiZn alloy core and a ZnO shell, is supported on the $Al_2O_3$, denoted as NixZny/$Al_2O_3$, where x:y=(1:1)-(1:4), representing the molar ratio of Ni/Zn.

Furthermore, the catalyst contains 1%-3% of Ni based on the mass of the $Al_2O_3$ support.

Still furthermore, the catalyst contains 0.5%-6% of Ni based on the mass of the $Al_2O_3$ support.

Furthermore, x:y=1:3.

According to another aspect of the present invention, a method for preparing the supported core-shell structured ZnO catalyst is provided, which is performed according to the following steps:

(1) dissolving $Ni(NO_3)_3·6H_2O$ and $Zn(NO_3)_2·6H_2O$ in deionized water;

(2) impregnating $Al_2O_3$ with the solution obtained in step (1), followed by uniform ultrasonic dispersion and complete drying; and (3) the solid obtained in the step (2) is calcinated at 500-600° C. for 2-4 h, followed by a reduction treatment to obtain a core-shell structured NiZn@ZnO catalyst supported on $Al_2O_3$.

Furthermore, the drying process in step (2) involves drying the mixture naturally at room temperature followed by drying at 80-100° C. until the mixture is completely dried.

Furthermore, the reduction treatment in step (3) is performed at 500-700° C. for 1-2 h.

According to yet another aspect of the present invention, a use of the supported core-shell structured ZnO catalyst in dehydrogenation of light alkanes to alkenes is provided.

Furthermore, the light alkane is propane, and the alkene is propylene.

The invention has the following beneficial effects:

According to the supported core-shell structured ZnO catalyst, the cheap and easily available non-noble metal oxide ZnO is taken as an active component, so that compared with the noble metal Pt-based catalysts commonly used in industry, the cost of the catalyst is greatly reduced. Besides, a NiZn@ZnO core-shell structure consisting of a NiZn alloy core and a ZnO shell is built by strong interaction (SMSI), and such strong interaction between NiZn alloy and ZnO along with electron transfer between NiZn alloy and ZnO can significantly change the geometry and electronic properties of ZnO so as to change the binding strength of the central active site O of ZnO to H during the dehydrogenation reaction. Therefore, the formation and desorption of $H_2O$ are inhibited, the reduction deactivation of ZnO is inhibited, and the supported core-shell structured ZnO catalyst has remarkably improved stability as compared with other reported ZnO-based dehydrogenation catalysts. It has been proved by several characterization methods that the NiZn alloy is completely encapsulated in the ZnO overlayer without Ni site exposed on the surface of the catalyst, thereby preventing the Ni sites with high C—C bond cleavage activity from detrimentally affecting the dehydrogenation selectivity, and maintaining the high selectivity of the ZnO-based dehydrogenation catalyst.

The catalyst provided by the present invention is prepared by co-impregnation methods with easily available raw materials, simple procedures, and high repeatability, exhibiting potential application value in industry.

The catalyst of the present invention shows promising catalytic performance in dehydrogenation of light alkanes to alkenes, with the conversion of light alkanes reaching more than 40% and the selectivity towards alkenes reaching more than 90% under a high-temperature condition. Meanwhile, the catalyst shows an excellent stability, breaking the limitation of rapid deactivation of the ZnO-based catalysts.

BRIEF DESCRIPTION OF THE DRAWINGS

FIG. 1 illustrates catalytic performance of catalysts prepared in Embodiments 1 to 6; where (a), and (b) show the conversion of $C_3H_6$ and selectivity of $C_3H_6$ as a function of time on stream over various NixZny/$Al_2O_3$, respectively, and (c) shows the comparison of deactivation rate constant over different catalysts.

FIG. 8 shows the DRIFTS spectra of catalysts prepared in Embodiments 1, 5 and 6 after CO chemisorption at 25° C. and subsequently purging with He for 30 min; where (a), (b) and (c) correspond to the catalysts prepared in Embodiment 5, Embodiment 1 and Embodiment 6, respectively.

FIG. 9 shows the catalytic activity as a function of the metallic surface area of Ni over the catalysts prepared in Embodiments 1, 2, 4, and 5; where (a) shows the metallic surface area of Ni of the catalysts prepared in Embodiments 1, 2, 4 and 5; and (b) shows conversion of propane as a function of the metallic surface area of Ni.

FIG. 10 shows the $H_2$-TPD profiles of the catalysts prepared in Embodiments 1 and 6; where (a) and (b) correspond to the catalysts prepared in Embodiment 6 and Embodiment 1, respectively.

DETAILED DESCRIPTION OF THE PRESENT INVENTION

The present invention is described in further detail by specific embodiments which enables those skilled in this field to fully understand the invention without limiting it in any way.

Embodiment 1

(1) 0.15 parts by mass of Ni(NO$_3$)$_3$·6H$_2$O and 0.45 parts by mass of Zn(NO$_3$)$_2$·6H$_2$O were dissolved in 1 mL of deionized water;
(2) 1 part by mass of $Al_2O_3$ was impregnated in the solution described above, the obtained system was subject to ultrasonic treatment for 0.5-1 h and naturally dried at room temperature for 12 h, and then completely dried at 80-100° C.;
(3) the solid obtained in step (2) was calcinated in air atmosphere at 600° C. for 3 h, and then it was reduced at 600° C. for 1 h to obtain the NiZn@ZnO core-shell structured catalyst supported on $Al_2O_3$, which contained 3% of Ni based on the mass of the support, named as Ni1Zn3/$Al_2O_3$;
(4) the prepared catalyst was ground and sieved to a certain size (20-40 mesh); and
(5) the prepared catalyst was loaded into a fixed-bed reactor, and the reaction was operated under a mixture of $C_3H_6$ and $H_2$ (molar ratio: 1:1) within $N_2$ as a balance gas. The weight hourly space velocity (WHSV) of propane was 4 h$^{-1}$.

Embodiment 2

This embodiment was carried out using the method described in Embodiment 1 for preparation and reaction with 0.45 parts by mass of Zn(NO$_3$)$_2$·6H$_2$O in step (1) being replaced by 0.15 parts by mass; and the catalyst contained 3% of Ni based on the mass of the support, named as Ni1Zn1/$Al_2O_3$.

Embodiment 3

This embodiment was carried out using the method described in Embodiment 1 for preparation and reaction with 0.45 parts by mass of Zn(NO$_3$)$_2$·6H$_2$O in step (1) being replaced by 0.6 parts by mass; and the catalyst contained 3% of Ni based on the mass of the support, named as Ni1Zn4/$Al_2O_3$.

Embodiment 4

This embodiment was carried out using the method described in Embodiment 1 for preparation and reaction with 0.45 parts by mass of Zn(NO$_3$)$_2$·6H$_2$O in step (1) being replaced by 0.05 parts by mass; and the catalyst contained 3% of Ni based on the mass of the support, named as Ni3Zn1/Al$_2$O$_3$.

Embodiment 5

This embodiment was carried out using the method described in Embodiment 1 for preparation and reaction with 0.45 parts by mass of Zn(NO$_3$)$_2$·6H$_2$O in step (1) being replaced by 0 parts by mass; and the catalyst contained 3% of Ni based on the mass of the support, named as Ni/Al$_2$O$_3$.

Embodiment 6

This embodiment was carried out using the method described in Embodiment 1 for preparation and reaction with 0.15 parts by mass of Ni(NO$_3$)$_3$·6H$_2$O in step (1) being replaced by 0 parts by mass, and the catalyst contained 10% of Zn based on the mass of the support, named as ZnO/Al$_2$O$_3$.

Embodiment 7

This embodiment was carried out using the method described in Embodiment 1 for preparation and reaction with 0.15 parts by mass of Ni(NO$_3$)$_3$·6H$_2$O in step (1) being replaced by 0.025 parts by mass, and the catalyst contained 0.5% of Ni based on the mass of the support, named as Ni1Zn3/Al$_2$O$_3$.

Embodiment 8

This embodiment was carried out using the method described in Embodiment 1 for preparation and reaction with 0.15 parts by mass of Ni(NO$_3$)$_3$·6H$_2$O in step (1) being replaced by 0.05 parts by mass, and the catalyst contained 1% of Ni based on the mass of the support, named as Ni1Zn3/Al$_2$O$_3$.

Embodiment 9

This embodiment was carried out using the method described in Embodiment 1 for preparation and reaction with 0.15 parts by mass of Ni(NO$_3$)$_3$·6H$_2$O in step (1) being replaced by 0.3 parts by mass, and the catalyst contained 6% of Ni based on the mass of the support, named as Ni1Zn3/Al$_2$O$_3$.

Embodiment 10

This embodiment was carried out using the method described in Embodiment 1 for preparation and reaction, and only differed in that in step (3), the calcination temperature was 400° C.

Embodiment 11

This embodiment was carried out using the method described in Embodiment 1 for preparation and reaction, and only differed in that in step (3), the calcination temperature was 500° C.

Embodiment 12

This embodiment was carried out using the method described in Embodiment 1 for preparation and reaction, and only differed in that in step (3), the calcination time was 2 h.

Embodiment 13

This embodiment was carried out using the method described in Embodiment 1 for preparation and reaction, and only differed in that in step (3), the calcination time was 4 h.

Embodiment 14

This embodiment was carried out using the method described in Embodiment 1 for preparation and reaction, and only differed in that in step (3), the reduction temperature was 500° C.

Embodiment 15

This embodiment was carried out using the method described in Embodiment 1 for preparation and reaction, and only differed in that in step (3), the reduction temperature was 700° C.

Embodiment 16

This embodiment was carried out using the method described in Embodiment 1 for preparation and reaction, and only differed in that in step (3), the reduction time was 2 h.

Figure 1A:
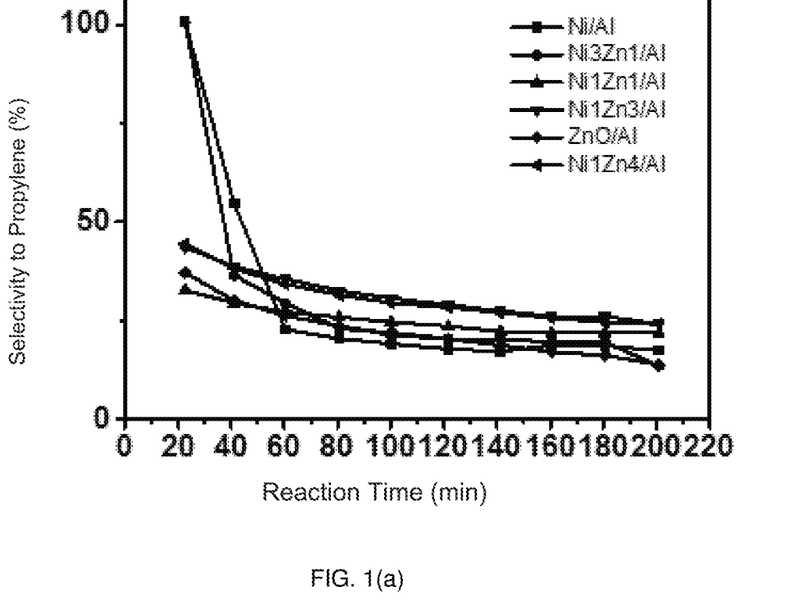
Figure 1B:
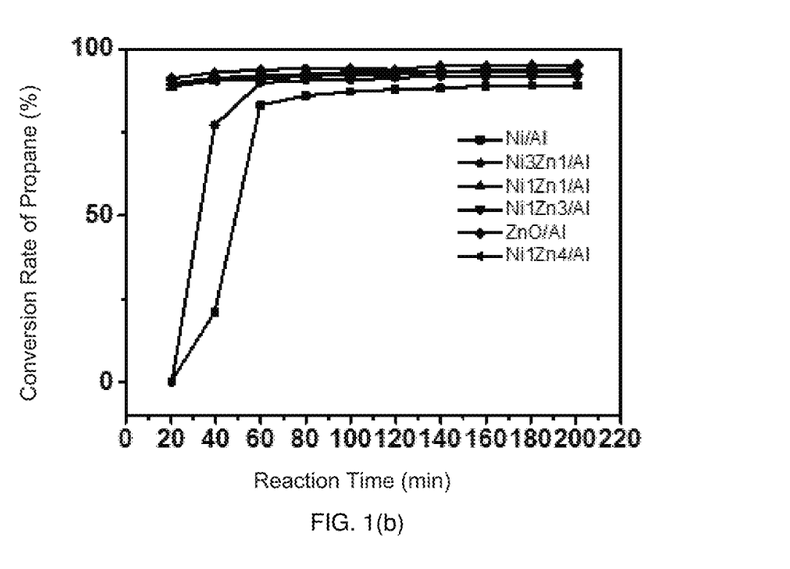
Figure 1C:
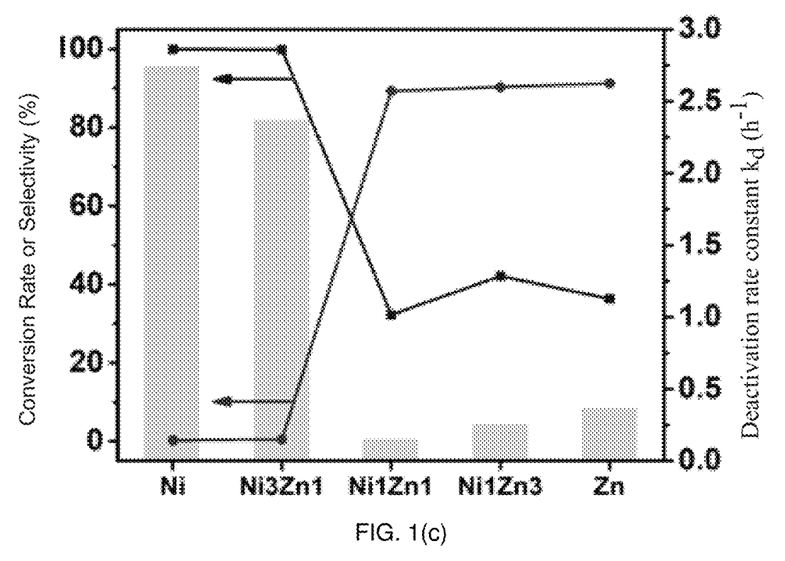

The catalysts prepared in the above embodiments were tested for catalytic performance in the propane dehydrogenation reaction, and the catalyst activity was expressed in terms of conversion of propane, selectivity of propylene, and deactivation rate, which will be discussed below in combination with the calculation results:

The catalysts of Embodiments 1 to 6 corresponding to different Ni/Zn ratios were tested for catalytic performance in propane dehydrogenation, and their catalytic performances were shown in FIG. 1, where (a), and (b) show the conversion of C$_3$H$_6$ and selectivity of C$_3$H$_6$ as a function of time on stream over various NixZny/Al$_2$O$_3$, respectively, and (c) shows the comparison of deactivation rate constant over different catalysts. As can be seen from FIG. 1, the NixZny/Al$_2$O$_3$ catalysts corresponding to Embodiments 1 to 3 performed well in catalytic stability; whereas pure Ni/Al$_2$O$_3$ of Embodiment 5 showed high initial activity, but poor selectivity to propylene and underwent an induction period during which rapid deactivation occurred due to the fast coke deposition covering the highly reactive sites, thereafter becoming relatively stable and low-active. The ZnO/Al$_2$O$_3$ of Embodiment 6 exhibited consistent high selectivity towards propylene but low activity with a propensity for continuous rapid deactivation with a deactivation rate constant (k$_d$) higher than 0.37 h$^{-1}$, indicating a poor stability during the propane dehydrogenation reaction. In addition, as can be seen from FIG. 1, with the increase of Zn addition, the catalytic behavior of NixZny/Al$_2$O$_3$ tended to transform from Ni-like to ZnO-like which may imply the transformation of active sites. For Ni1Zn3/Al$_2$O$_3$, the deactivation tendency was significantly suppressed and higher activity together with similar selectivity was achieved when compared with ZnO/Al₂O₃, with an initial conversion of propane of 37%, and a selectivity of propene of more than 90%.

Figure 2:
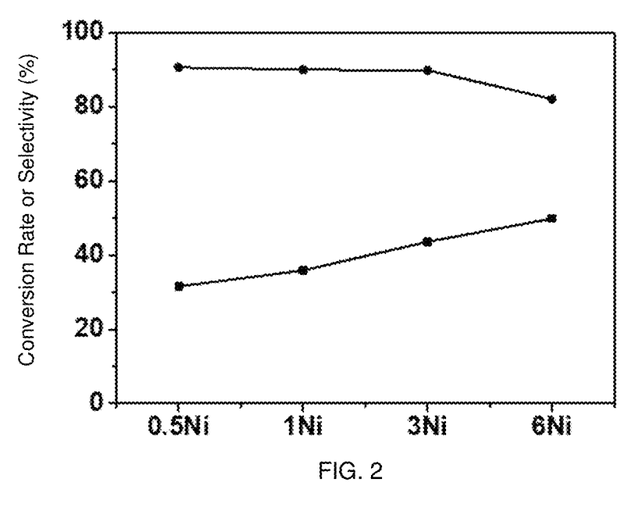
FIG. 2 shows catalytic performance of catalysts prepared in Embodiments 1, 7, 8 and 9.

Embodiments 1, 7, 8 and 9 provide catalysts prepared with different Ni loadings (based on the mass of the support) and their catalytic performance in propane dehydrogenation. It can be seen from FIG. 2 that the conversion of propane increased gradually with the increase of Ni loading. But the selectivity to propylene dropped dramatically as the Ni loading increased to 6 wt %, which can be attributed to the partial exposure of Ni sites resulting from the higher Ni content. The catalytic performance was optimal when the content of Ni was 3 wt %.

Figure 3:
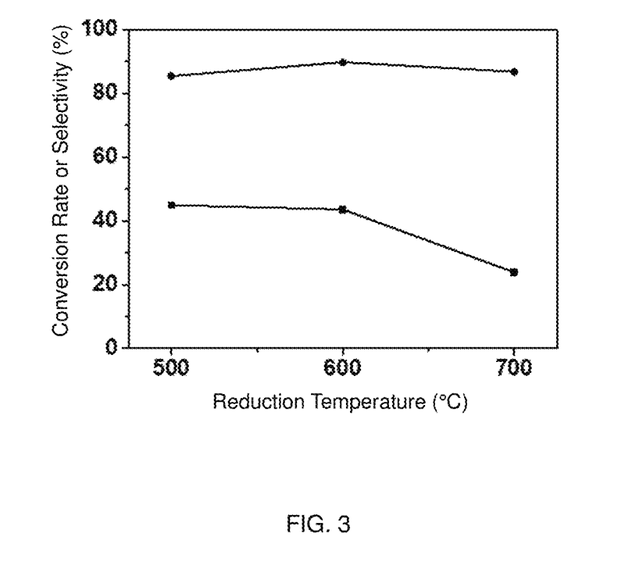
FIG. 3 shows catalytic performance of Ni1Zn3/$Al_2O_3$ catalysts prepared in Embodiments 1, 14 and 15.

Embodiments 1, 14 and 15 provide catalysts prepared at different reduction temperatures and their catalytic performance in propane dehydrogenation. It can be seen from FIG. 3 that there was no significant change in the catalytic performance when the reduction temperature was between 500° C. and 600° C., but the conversion of propane decreased significantly when the reduction temperature was increased to 700° C., which can be explained by the deep reduction of ZnO as an active species, forming metallic Zn with a lower melting point (420° C.) and no activity for propane dehydrogenation, resulting in the decrease in activity.

Figure 4:
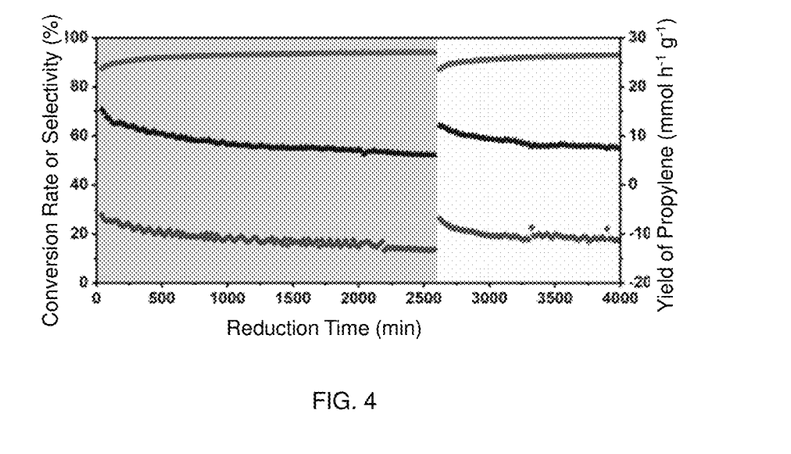
FIG. 4 is a graph showing the result of a regeneration stability test at 550° C. over the Ni1Zn3/$Al_2O_3$ catalyst prepared in Embodiment 1.

The catalyst prepared in Embodiment 1 was further subject to a long-term regeneration stability test at 550° C., and the result is shown in FIG. 4. While maintaining a stable selectivity of more than 90%, the deactivation rate constant ($k_d$) of the Ni1Zn3/Al₂O₃ catalyst was as low as 0.017 h$^{-1}$, indicating excellent long-term stability, breaking the limitation of rapid deactivation of ZnO-based catalysts.

Figure 5:
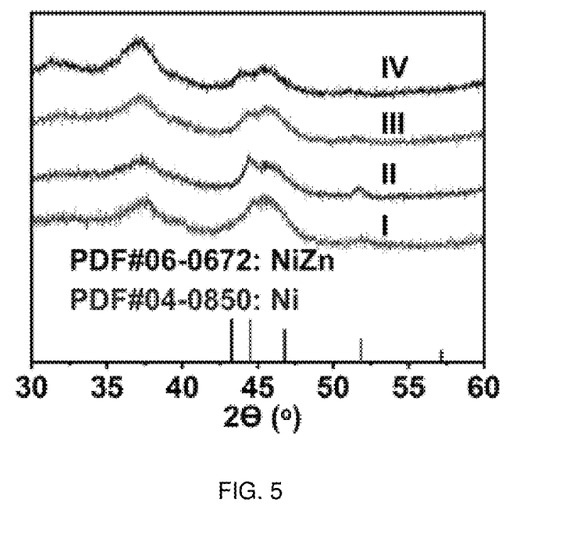
FIG. 5 shows XRD patterns of the catalysts prepared in Embodiments 1, 2, 4 and 5, where I, II, III and IV correspond to Embodiments 5, 4, 2 and 1, respectively.

XRD analysis was performed over the catalysts of Embodiments 1, 2, 4 and 5 with different Ni/Zn ratios, and the resulting patterns are shown in FIG. 5, where I, II, III and IV correspond to Embodiments 5, 4, 2 and 1, respectively. the transformation trend from Ni(111) to NiZn (101) can be clearly observed with the increase of Zn addition, indicating Zn incorporating into the bulk phase of Ni and the formation of NiZn alloy.

Figure 6:
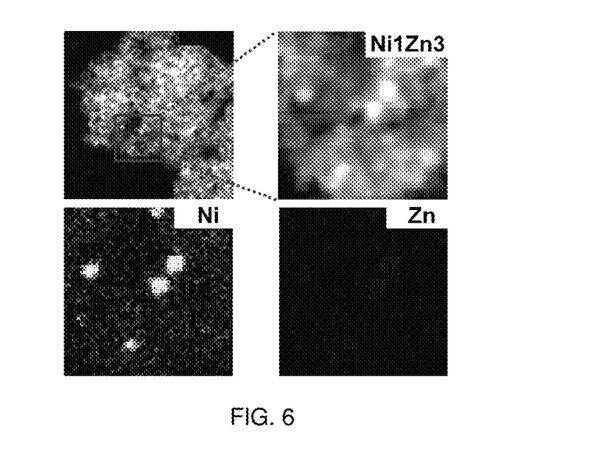
FIG. 6 shows the EDS-mapping image of the Ni1Zn3/$Al_2O_3$ catalyst prepared in Embodiment 1.

EDS-mapping analysis was performed over the Ni1Zn3/Al₂O₃ catalyst prepared in Embodiment 1, and the images are shown in FIG. 6. The uniform Ni—Zn element distribution over Al₂O₃ support excluded the possibility of phase separation, implying the surface segregation of certain form of Zn species during the formation of NiZn alloy nanoparticles.

Figure 7:
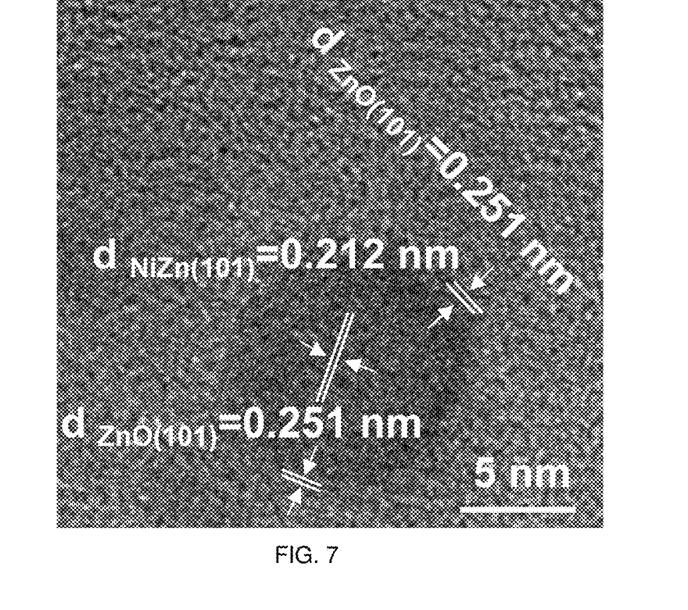
FIG. 7 shows the TEM image of the Ni1Zn3/$Al_2O_3$ catalyst prepared in Embodiment 1.

Also referring to FIG. 7, the Ni1Zn3/Al₂O₃ catalyst prepared in Embodiment 1 was analyzed by high-resolution TEM. The existence of homogenous ZnO overlayers on the surface of bulk NiZn alloy nanoparticles was discovered through the identification of lattice fringes, establishing a NiZn@ZnO core-shell nanostructure.

Figure 8A:
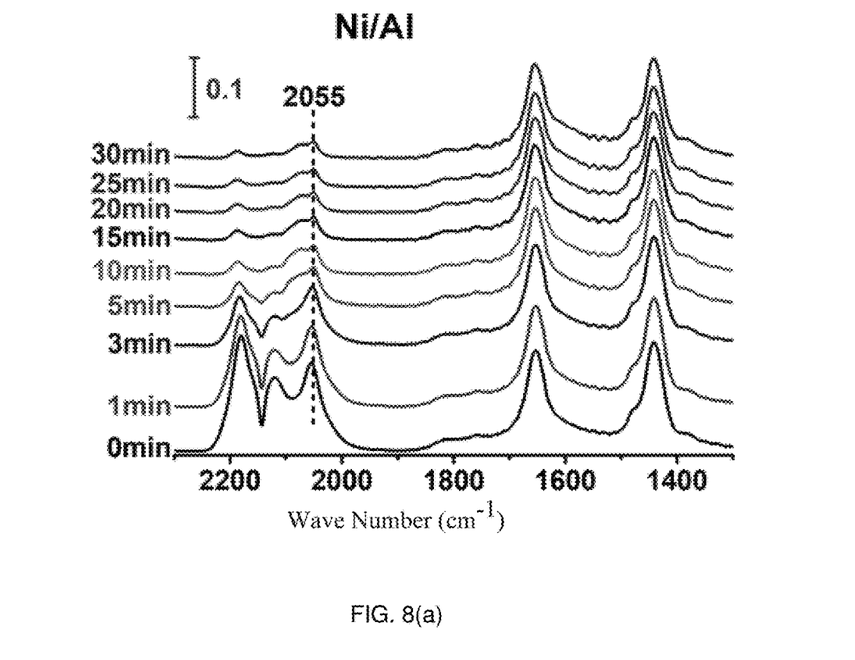
Figure 8B:
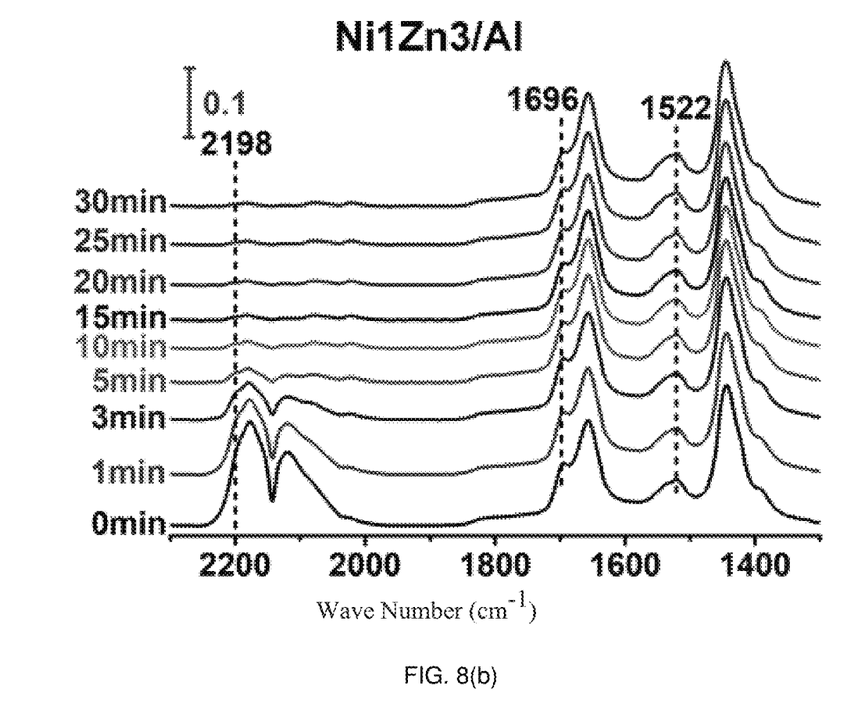
Figure 8C:
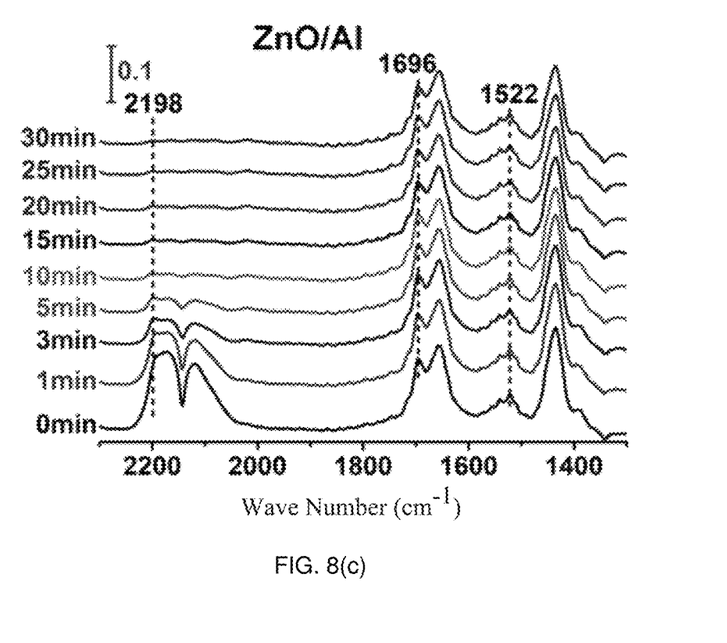

Surface-sensitive DRIFTS measurements using CO adsorption as a probe were performed on the catalysts prepared in Embodiments 1, 5 and 6, and the results are shown in FIG. 8, where (a), (b) and (c) correspond to the catalysts prepared in Embodiments 5, 1 and 6, respectively. It was found that the CO adsorption peak on Ni at 2055 cm$^{-1}$ disappeared over Ni1Zn3, while a CO linear adsorption peak on ZnO appeared at 2198 cm$^{-1}$, together with adsorption peaks of some carbonate species on ZnO at 1696 and 1522 cm$^{-1}$, validating the reverse encapsulation of ZnO on Ni induced by strong metal-oxide interaction.

Figure 9A:
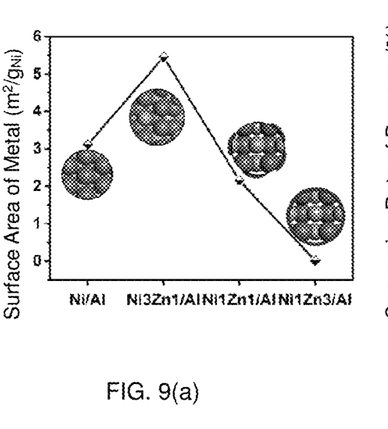
Figure 9B:
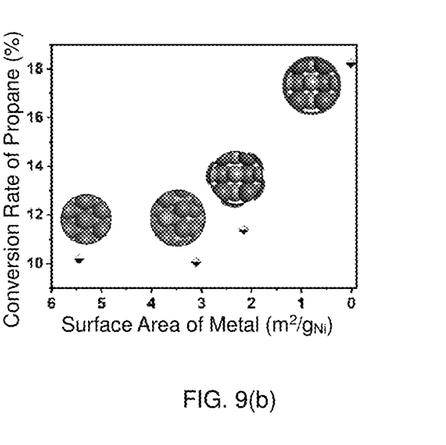

Furthermore, H₂ pulse chemisorption experiments were performed over the catalysts prepared in Embodiments 1, 2, 4 and 5 to measure the active metallic Ni surface area H₂ pulse chemisorption experiments were performed over the catalysts prepared in Embodiments 1, 2, 4 and 5 to measure the active metallic Ni surface area, as shown in FIG. 9, where (a) displays the metallic surface area of Ni; and (b) displays conversion of propane as a function of the metallic surface area of Ni. The active metallic Ni surface area firstly increased and then gradually decreased to near zero with the increase of Zn addition. The increase could be due to the initial formation of NiZn alloy, which improved the dispersion of Ni. However, further addition of Zn gave rise to ZnO overlayers forming on the surface of NiZn alloy, leading to the reduction of metallic surface area of Ni. The near zero value of metallic Ni surface area for Ni1Zn3/Al₂O₃ and the simultaneous reaching of the highest propane conversion confirmed the successful construction of the NiZn@ZnO core-shell structure without Ni exposure on the surface. This result excluded the assumption of Ni sites directly participating in the reaction, which meant Ni exclusively acted as a promoter while ZnO overlayers functioned as the active sites for propane dehydrogenation.

Figure 10A:
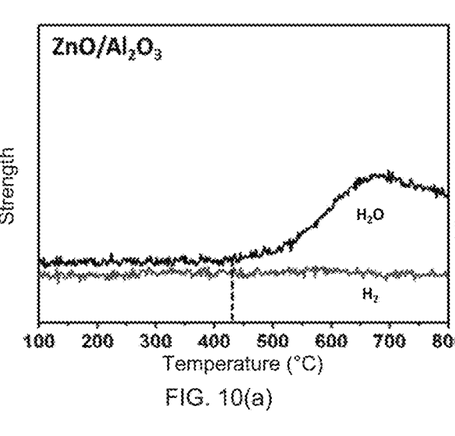
Figure 10B:
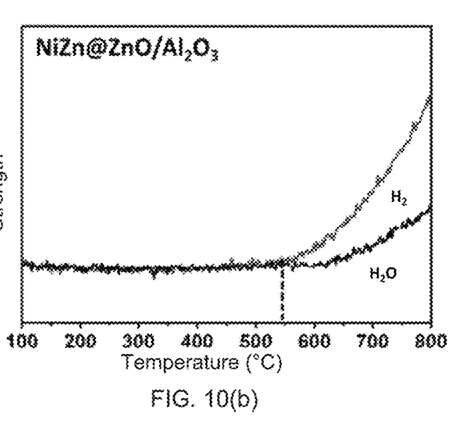

H₂-TPD tests were performed on the catalysts prepared in Embodiments 1 and 6, and the results are shown in FIG. 10, where (a) and (b) correspond to the catalysts prepared in Embodiments 6 and 1, respectively. These results can explain the inhibited deactivation of the ZnO species over NiZn@ZnO. The core-shell structure induced by strong metal-oxide interaction changes the geometric environment of Zn and O sites and concomitant electron transfer from the ZnO shell to the alloy core reduces the electron density of O sites, which weakens O—H binding and thus facilitates the dissociation of O—H bond in preference to dissociation of Zn—OH bond over surface ZnO, accelerating H₂ desorption and therefore retarding the reduction of ZnO during reaction.

Although the preferred embodiments of the present invention have been described above with reference to the accompanying drawings, the present invention is not limited to the embodiments described above, which are intended to be illustrative and not restrictive, enlightened by the present invention, those skilled in this field can make many specific changes without departing from the purpose of the present invention and the protection scope of the claims, and these all fall within the protection scope of the present invention.

What is claimed is:

1. A supported core-shell structured ZnO catalyst, wherein the catalyst is composed of Al₂O₃ as a support and ZnO as active sites; a NiZn@ZnO core-shell structure, which consists of a NiZn alloy core and a ZnO shell, is supported on the Al₂O₃, denoted as NixZny/Al₂O₃, wherein x:y=(1:1)-(1:4), representing the molar ratio of Ni/Zn.

2. The supported core-shell structured ZnO catalyst according to claim 1, wherein the catalyst contains 1%-3% of Ni based on the mass of the Al₂O₃ support.

3. The supported core-shell structured ZnO catalyst according to claim 2, wherein the catalyst contains 0.5%-6% of Ni based on the mass of the Al₂O₃ support.

4. The supported core-shell structured ZnO catalyst according to claim 1, wherein x:y=1:3.

5. A method for preparing the supported core-shell structured ZnO catalyst according to claim 1, wherein the method comprises the following steps:
   (1) dissolving Ni(NO₃)₃·6H₂O and Zn(NO₃)₂·6H₂O in deionized water;
   (2) impregnating Al₂O₃ with the solution obtained in step (1), followed by uniform ultrasonic dispersion and complete drying; and
   (3) the solid obtained in step (2) being calcinated at 500-600° C. for 2-4 h, followed by a reduction treatment to obtain a core-shell structured NiZn@ZnO catalyst supported on $Al_2O_3$.

6. The method for preparing the supported core-shell structured ZnO catalyst according to claim 5, wherein the drying process in step (2) involves drying the mixture naturally at room temperature followed by drying at 80-100° C. until the mixture is completely dried.

7. The method for preparing the supported core-shell structured ZnO catalyst according to claim 5, wherein the reduction treatment in step (3) is performed at 500-700° C. for 1-2 h.

8. The method of claim 5, wherein the catalyst contains 1%-3% of Ni based on the mass of the $Al_2O_3$ support.

9. The method of claim 8, wherein the catalyst contains 0.5%-6% of Ni based on the mass of the $Al_2O_3$ support.

10. The method of claim 5, wherein x:y=1:3.

11. A use of the supported core-shell structured ZnO catalyst according to claim 1 in dehydrogenation of light alkanes to alkenes.

12. The use of the supported core-shell structured ZnO catalyst in dehydrogenation of light alkanes to alkenes according to claim 11, wherein the light alkane is propane, and the alkene is propylene.

13. The use of the supported core-shell structured ZnO catalyst of claim 11, wherein the catalyst contains 1%-3% of Ni based on the mass of the $Al_2O_3$ support.

14. The use of the supported core-shell structured ZnO catalyst of claim 13, wherein the catalyst contains 0.5%-6% of Ni based on the mass of the $Al_2O_3$ support.

15. The use of the supported core-shell structured ZnO catalyst of claim 11, wherein x:y=1:3.

* * * * *